United States Patent [19]
Langdon et al.

[11] Patent Number: 5,665,452
[45] Date of Patent: Sep. 9, 1997

[54] THREE-DIMENSIONAL, MACROSCOPICALLY EXPANDED, APERTURED LAMINATE WEBS

[75] Inventors: Fred M. Langdon; G. Chris Dobrin, both of Cincinnati, Ohio

[73] Assignee: The Procter & Gamble Company, Cincinnati, Ohio

[21] Appl. No.: 205,968

[22] Filed: Mar. 3, 1994

[51] Int. Cl.⁶ .................. B32B 5/12; B32B 3/10; B27N 3/00
[52] U.S. Cl. .......... 428/131; 428/109; 428/137; 428/138; 428/141; 428/318.4; 156/62.4; 156/62.6; 156/62.8; 156/275.5; 442/62; 442/396; 442/398
[58] Field of Search ............ 428/109, 131, 428/137, 224, 247, 284, 285, 296, 318.4, 138, 141; 156/62.4, 62.6, 62.8, 272.6, 272.3, 272.5, 275.5, 307.3, 307.7, 308.4

[56] References Cited

U.S. PATENT DOCUMENTS

| | | | |
|---|---|---|---|
| 3,043,738 | 7/1962 | Demeter et al. | 156/229 |
| 3,077,882 | 2/1963 | Trewella | 128/156 |
| 3,081,515 | 3/1963 | Griswold et al. | 28/78 |
| 3,165,432 | 1/1965 | Plaskett | 156/244 |
| 3,190,781 | 6/1965 | Metz, Jr. | 156/244 |
| 3,331,728 | 7/1967 | Lane | 161/112 |
| 3,421,964 | 1/1969 | Arbit | 156/244 |
| 3,523,149 | 8/1970 | Hartmann | 264/90 |
| 3,878,014 | 4/1975 | Melead | 156/167 |
| 3,911,186 | 10/1975 | Trotman | 428/137 |
| 3,929,135 | 12/1975 | Thompson | 128/287 |
| 3,945,386 | 3/1976 | Anczurowski et al. | 128/287 |
| 3,965,906 | 6/1976 | Karami | 128/287 |
| 3,967,623 | 7/1976 | Butterworth et al. | 128/287 |
| 3,987,792 | 10/1976 | Hernandez et al. | 128/284 |
| 3,994,299 | 11/1976 | Karami | 128/287 |
| 4,077,410 | 3/1978 | Butterworth et al. | 128/287 |
| 4,323,069 | 4/1982 | Ahr et al. | 128/287 |
| 4,342,314 | 8/1982 | Radel et al. | 128/287 |
| 4,609,518 | 9/1986 | Curro et al. | 264/504 |
| 4,619,724 | 10/1986 | Chatow | 156/72 |
| 4,695,422 | 9/1987 | Curro et al. | 264/504 |
| 4,726,976 | 2/1988 | Karami et al. | 428/137 |
| 4,781,962 | 11/1988 | Zamarripa et al. | 428/138 |
| 4,995,930 | 2/1991 | Merz et al. | 156/209 |
| 5,066,494 | 11/1991 | Becher | 424/448 |
| 5,171,238 | 12/1992 | Kajander | 604/383 |
| 5,173,351 | 12/1992 | Ruppel et al. | 428/1.74 |
| 5,368,910 | 11/1994 | Langdon | 428/137 |

FOREIGN PATENT DOCUMENTS

| | | | |
|---|---|---|---|
| 0 040 084 | 11/1981 | European Pat. Off. | A61F 13/00 |
| 0 295 694 | 12/1988 | European Pat. Off. | |
| 0 545 423 A1 | 6/1993 | European Pat. Off. | A61F 13/15 |
| 982757 | 2/1965 | United Kingdom | |
| 93/09741 | 5/1993 | WIPO | A61F 13/15 |
| 93/22995 | 11/1993 | WIPO | A61F 13/15 |

*Primary Examiner*—Thurman K. Page
*Assistant Examiner*—Kathryne E. Shelborne
*Attorney, Agent, or Firm*—William Scott Andes; Roddy M. Bullock; E. Kelly Linman

[57] ABSTRACT

The present invention provides a three-dimensional, macroscopically expanded, apertured, laminate web suitable for use as a topsheet on an absorbent article and a method for making the same. The web includes a first layer of substantially transparent, polymeric material having an inner surface and an outer surface. A nonwoven web is secured to the inner surface of the substantially transparent polymeric material and is visible through the substantially transparent polymeric material. The presence of the nonwoven web creates the appearance of a fibrous web which is perceived as soft and skin friendly while still maintaining the fluid transport benefits of prior art plastic webs.

4 Claims, 5 Drawing Sheets

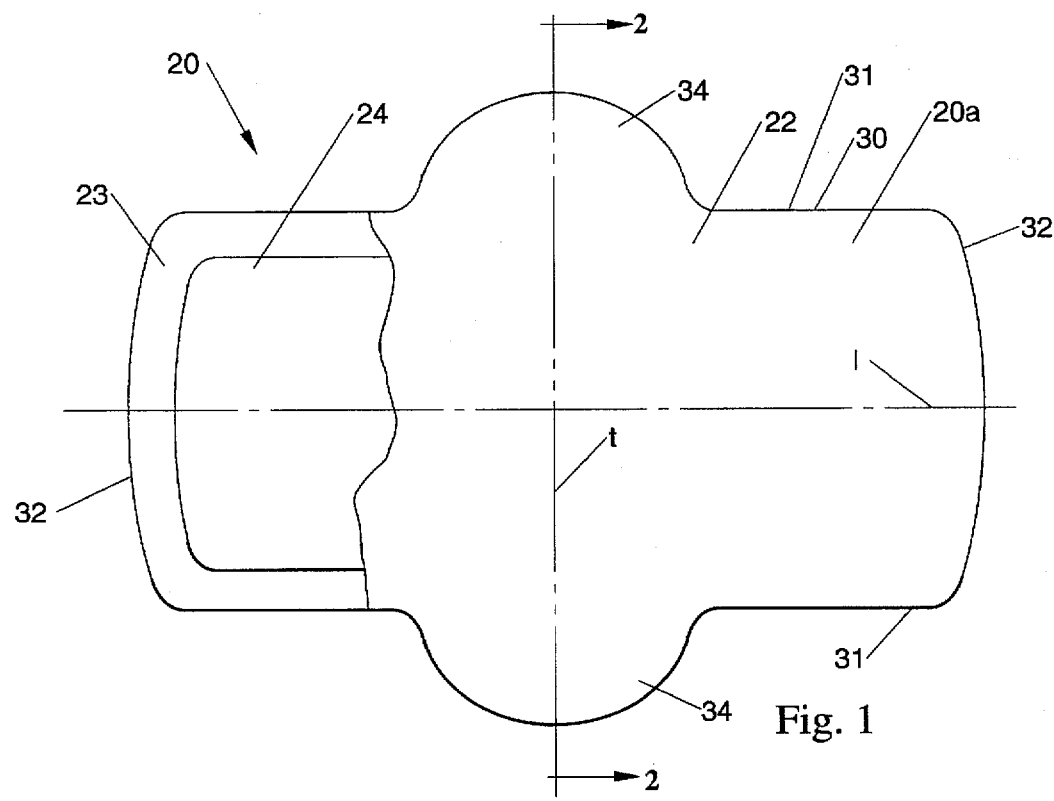
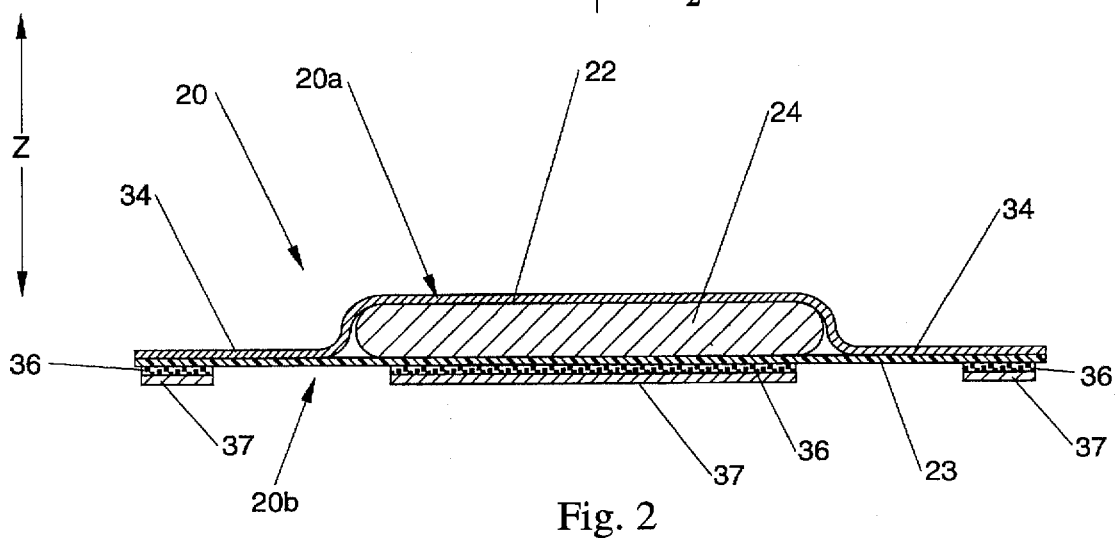

THREE-DIMENSIONAL, MACROSCOPICALLY EXPANDED, APERTURED LAMINATE WEBS

TECHNICAL FIELD

The present invention relates to laminate webs, and more particularly, the present invention relates to three-dimensional, macroscopically expanded, apertured, laminate webs for use as topsheets on absorbent articles, especially catamenial articles.

The present invention also relates to a method for making a three-dimensional, macroscopically expanded, apertured, laminate web.

BACKGROUND OF THE INVENTION

It has long been known in the disposable absorbent bandage art that it is extremely desirable to construct absorptive devices such as disposable diapers, catamenials, sanitary napkins, incontinent articles, and the like, presenting a dry surface feel to the user to improve wearing comfort and to minimize the development of undesirable skin conditions due to prolong exposure to moisture absorbed within the absorbent article.

One viable prior art solution to the aforementioned problem is disclosed in commonly assigned U.S. Pat. No. 4,342, 314 issued to Radel et al. on Aug. 3, 1982 and hereby incorporated herein by reference. Radel et al. discloses an absorbent article with a wearer-contacting topsheet comprising a resilient, macroscopically expanded, three-dimensional, plastic web exhibiting a combination of fiber-like and plastic properties. In a preferred embodiment, the macroscopically expanded, three-dimensional, plastic web topsheet disclosed in Radel et al. exhibits a fine scale three-dimensional microstructure comprising a regulated continuum of capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel et al. structure comprises an uppermost capillary opening or aperture formed by a multiplicity of fiber-like elements interconnected to one another in the uppermost plane of the web. Each of the fiber-like elements exhibits a substantially uniform U-shaped cross-section along its length. The cross-section of the fiber-like elements comprises a base portion located in the wearer-contacting plane and a sidewall portion joined to each edge of the base portion. The sidewall portions extend generally in the direction of the absorbent pad-contacting surface of the web. The sidewall portions which intersect one another are joined to one another intermediate the wearer-contacting surface and the absorbent pad-contacting surface of the web, thereby forming a capillary network interconnecting the opposed surfaces of the web.

A topsheet of the type generally disclosed by Radel et al. is highly effective in promoting rapid fluid transport from the first or wearer-contacting surface to the second or absorbent pad-contacting surface of the topsheet. Accordingly, topsheets of this type have enjoyed widespread commercial success on catamenial pads due to their clean and dry appearance in use when contrasted to conventional nonwoven fibrous topsheets. Although effective in the transfer of bodily fluids away from the wearer's skin, it has been learned that some users find it psychologically and/or physically undesirable to employ a material which is perceived as plastic in direct contact with their skin.

SUMMARY OF THE INVENTION

The present invention pertains, in a preferred embodiment, to a process for forming a three-dimensional, macroscopically expanded, apertured, fluid previous web having a first surface and a second surface. The web is comprised of a first layer of polymeric material and a second nonwoven web secured to and underlying the first layer of polymeric material. A nonwoven web is fed onto a forming structure, having opposed surfaces. The forming structure exhibits a multiplicity of apertures which place the opposed surfaces of the forming structure in fluid communication with one another. A molten resin is extruded onto said nonwoven web. A vacuum is applied across the thickness of the nonwoven web and the extruded resin. The vacuum is sufficiently great enough to cause the web and the resin to be secured together, to rupture in those areas coinciding with the apertures in the forming structure, and to conform with the forming structure.

The present invention also pertains, in another preferred embodiment, to a process for forming a three-dimensional, macroscopically expanded, apertured, fluid previous web having a first surface and a second surface. The web is comprised of a first layer of polymeric material and a second nonwoven web secured to and underlying the first layer of polymeric material. A nonwoven web is fed onto a first forming structure having opposed surfaces. The first forming structure exhibits a multiplicity of apertures which place the opposed surfaces of the first forming structure in fluid communication with one another. A molten resin is extruded onto said nonwoven web. A vacuum is applied across the thickness of the nonwoven web and the extruded resin. The vacuum is sufficiently great to cause the extruded resin to bond with the nonwoven web creating a laminate web. The laminate web is fed onto a second forming structure having opposed surfaces. The second forming structure exhibits a multiplicity of apertures which place the opposed surfaces of the second forming structure in fluid communication with one another. A fluid pressure differential is applied across the thickness of the laminate web. The fluid pressure differential is sufficiently great to cause the laminate web to rupture in those areas coinciding with the apertures in the second forming structure and to conform with the forming structure.

The present invention also pertains, in another preferred embodiment to a process for forming a three-dimensional, macroscopically expanded, apertured, fluid previous web having a first surface and a second surface. The web is comprised of a first layer of polymeric material and a second nonwoven web secured to and underlying said first layer of polymeric material. A nonwoven web is fed onto a forming structure having opposed surfaces. The forming structure exhibits a multiplicity of apertures which place the opposed surfaces of said forming structure in fluid communication with one another. A fluid pressure differential is applied across the thickness of said nonwoven web. The fluid pressure differential is sufficiently great to cause said nonwoven web to rupture in those areas coinciding with said apertures in said forming structure and to conform with said forming structure. A polymeric resin is fed onto said nonwoven web. A fluid pressure differential is then applied across the thickness of said resin and said nonwoven web. The fluid pressure differential is sufficiently great to cause said nonwoven web and said resin to be secured together and to rupture said resin in those areas coinciding with said apertures in said forming structure and to conform with said forming structure.

The present invention also pertains to a three-dimensional, macroscopically expanded, fluid previous web suitable for use as a topsheet on an absorbent article. The web has a first surface and a second surface which are located in planes remote from one another. The web includes a first layer of substantially transparent, polymeric material. The first layer has an inner surface and an outer surface. A nonwoven web is secured to the inner surface of the first layer of substantially transparent polymeric material. The nonwoven web is visible through the first layer of substantially transparent polymeric material. A plurality of capillaries extend from the first surface of the web to the second surface of the web for the transmission of fluids through the web. Each of the capillaries originates as an aperture in the first surface of the web and has a continuously interconnected sidewall portion between the first and second surfaces. The continuously interconnected sidewalls terminate to form an aperture in the second surface.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein;

FIG. 1 is a top plan view of a sanitary napkin with portions of the sanitary napkin cut-away to more clearly show the construction of the sanitary napkin;

FIG. 2 is cross-sectional view of the sanitary napkin of FIG. 1 taken along section line 2—2;

DETAILED DESCRIPTION OF THE INVENTION

Figure 3:
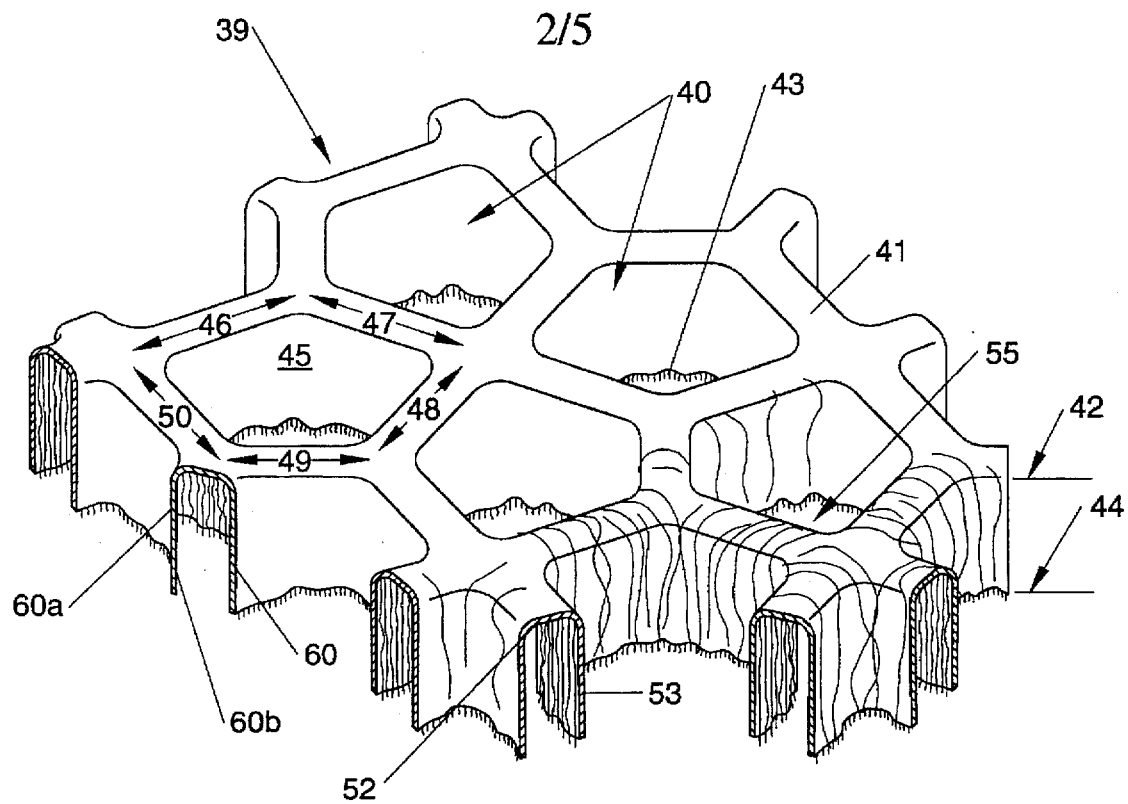
FIG. 3 is an enlarged, partially segmented, perspective illustration of a preferred embodiment of a three-dimensional, macroscopically expanded, apertured, laminate web of the present invention.

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

A preferred embodiment of a unitary disposable absorbent article is the catamenial pad, the sanitary napkin 20 shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, incontinence pads, and the like.

Sanitary napkin 20 has two surfaces, a wearer-contacting surface or body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "1" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the sanitary napkin being cut-away to more clearly show the construction of the sanitary napkin 20 and with the portion of the sanitary napkin 20 which faces or contacts the wearer 20a oriented towards the viewer. As shown in FIG. 1, the sanitary napkin 20 preferably comprises a liquid previous topsheet 22, a liquid impervious backsheet 23 joined with the topsheet 22, and an absorbent core 24 positioned between the topsheet 22 and the backsheet 23.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

The sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

FIG. 2 is a cross-sectional view of the sanitary napkin 20 taken along section line 2—2 of FIG. 1. As can be seen in FIG. 2 the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "Z" direction or axis, which is the direction preceding down through the topsheet 22 and into whatever fluids storage core 24 that may be provided. The objective is to provide a continuous path between the topsheet 22 and underlying layer or layers of the absorbent articles herein, such that fluid is eventually drawn in the "Z" direction and away from the topsheet of the article and into its ultimate storage layer. In a preferred embodiment, the continuous path will have a gradient of increasing capillary attraction which facilitates fluid flow down and into the storage medium.

FIG. 3 is an enlarged partially segmented; perspective illustration of a preferred embodiment of a macroscopically expanded, three-dimensional, fiber-like, apertured, laminate web 39 which has been found suitable for use as a topsheet 22 on sanitary napkin 20. The term "macroscopically expanded", when used to describe three-dimensional webs of the present invention, refers to webs, ribbons, and films which have been caused to conform to the surface of a three-dimensional forming structure so that both surfaces thereof exhibit a three-dimensional pattern of surface aberrations corresponding to the macroscopic cross-section of said forming structure. The surface aberrations comprising said pattern being individually discernible to the normal naked eye, i.e., a normal naked eye having 20/20 vision unaided by any instrument that changes the apparent size or distance of an object or otherwise alters the visual powers of the eye, when the perpendicular distance between the viewer's eye and the plane of the web is about 12 inches. The term "fiber-like" as utilized herein to describe the appearance of webs of the present invention, refers generally to any fine scale pattern of apertures, random or non-random, reticulated or non-reticulated, which connotes an overall appearance and impression of a woven or nonwoven fibrous web when viewed by the human eye. As can be seen in FIG. 3, the web's fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 40. The web 39, which exhibits a fiber-like appearance, embodies a three-dimensional microstructure extending from the web's uppermost or wearer-contacting surface 41 in plane 42 to its lowermost or absorbent pad-contacting surface 43 in plane 44, to promote rapid fluid transport from the uppermost surface 41 to the lowermost surface 43 of the web without lateral transmission of fluids between adjacent capillaries 40. As utilized herein, the term "microstructure" refers to a structure of such fine scale that its precise detail is readily perceived by the human eye only upon magnification by a microscopic or other means well-known in the art.

Apertures 45 are formed by a multiplicity of intersecting fiber-like elements, e.g., elements 46, 47, 48, 49 and 50, interconnected to one another in the first surface of the web. Each fiber-like element comprises a base portion, e.g., base portion 52, located in plane 42. Each base portion has a sidewall portion, e.g., sidewall portions 53, attached to each edge thereof. The sidewall portions 53 extend generally in the direction of the second surface 43 of the web. The intersecting sidewall portions of the fiber-like elements are interconnected to one another intermediate the first and second surfaces of the web and terminate substantially concurrently with one another in the plane 44 of the second surface.

In a particularly preferred embodiment, the interconnected sidewall portions terminate substantially concurrently with one another in the plane of the second surface 44 to form apertures 55 in the second surface 43 of the web. The network of capillaries 40 formed by the interconnected sidewall portions allows for free transfer of fluids from the first surface of the web directly to the second surface of the web without lateral transmission of the fluid between adjacent capillaries.

The web 39 is comprised of a first, top or uppermost layer 60, and a second, bottom or lowermost layer 62. The uppermost layer has an outer or exposed surface 60a and an inner surface 60b. The lowermost layer 62 is secured to the inner surface 60b of the uppermost layer 60. The uppermost layer 60 is preferably formed from a thermoplastic material, e.g., polyethylene, polypropylene, ethylene vinyl acetate (EVA) or any combination of the above materials. The uppermost layer 60 may also be a co-extruded combination of any of the above-mentioned materials. Preferably, the materials used for the co-extruded uppermost layer 60 enable the inner surface layer 60b of the uppermost layer 60 to be thermally bonded to the lowermost layer 62. The lowermost layer 62 is preferably a relatively low basis weight, lightly bonded non-woven web of synthetic fibers, such as nylon, polyethylene, polypropylene, polyester, hi-component binder fibers, or natural fibers, such as cellulosic fibers or any combination of the above. The shape of the fibers can be of any configuration or cross-section such as round, oval, square, rectangular, star, etc.

The second or lowermost 62 is preferably a relatively thin layer that substantially follows the contours of the inner surface 60b of the uppermost layer 60. Accordingly, a large portion of the space created within the inner portion of a fiber-like element remains open or unobstructed, i.e., the inner portion is substantially free of fibers from the lowermost layer 62. This may be important when the sanitary napkin is exposed to large volumes of bodily fluids and the absorbent core becomes saturated. The fluid may be held in the inner spaces provided in the fiber-like elements.

The fibers of the lowermost layer 62 preferably extend below the second surface 43 of the web 39. Preferably, when web 39 is used as a topsheet, lowermost layer 62 of fibrous material is in fluid transporting contact with the absorbent core 24 located immediately adjacent and underneath topsheet 22. In use, bodily fluids will initially impinge the first surface 41 of the laminate web 39. The fluid will then move through the capillaries 40 from the first or uppermost surface 41 to the second or lowermost surface 43. As fluid reaches apertures 55 in the lowermost surface of the web 39 it contacts the fibrous material of lowermost layer 62. The fibers of lowermost layer 62 break the fluid meniscuses which tend to form along the second surface 43 of the web 39 allowing the capillaries 40 to completely drain. By draining the capillaries of bodily fluids, the web 39 provides a drier and cleaner topsheet 22. By draining substantially all of the fluid within the network of capillaries 40, the web 39 is essentially renewed for the next infusion of bodily fluids.

In addition to breaking up the fluid meniscuses along the second surface of the web, the fibrous material of lowermost layer 62 may provide better fluid integration with the absorbent core 24 through fiber entanglement of the fibrous material of the absorbent core 24 and the fibrous material of the lowermost layer 62.

By improving fluid integration between the topsheet and the underlying absorbent core a more dependable fluid passageway is created as opposed to conventional adhesives or thermal bonding. Conventional adhesives if applied too strongly have a tendency to block the fluid passageways in the capillaries thus preventing the capillaries from properly draining and emptying the bodily fluids into the underlying absorbent core. In addition, excessive use of adhesives tends to create a stiff, rigid absorbent article which is neither comfortable or effective in its use to absorb bodily fluids. Conventional thermal bonding melts together the topsheet and core by partially destroying selected portions of each in the melting or fusing process. These destroyed portions are rendered impervious to the passage of fluids.

By providing a continuous path for bodily fluids between the topsheet and the adjacent underlying layer, e.g., the secondary topsheet or absorbent core, the topsheet is renewed for the next infusion of bodily fluid, thereby leaving the topsheet with a fresh, dry appearance and feel. The sanitary napkin 20 is then able to continue to receive fluid until the absorbent core 24 becomes saturated.

In a particularly preferred embodiment; the uppermost layer 60 is transparent or clear. In other words, the uppermost layer 60 is substantially free of pigments, e.g., titanium dioxide, that are often used to whiten the plastic film. By having the uppermost layer 60 transparent or clear the fibrous material of the lowermost layer 62 is readily visible to the naked eye through the uppermost layer 60, thereby providing the appearance of a nonwoven web or cloth like material. By providing a material which has the appearance of a nonwoven web, the topsheet will have a less plastic like appearance and accordingly the topsheet may present a more user friendly surface as compared to conventional opaque plastic topsheets.

The various layers of the macroscopically expanded web 39 may be treated with certain finishes or resins in order to enhance certain fluid properties. Preferably, the uppermost layer has a generally hydrophobic finish as compared with the lowermost layer 62 which is generally preferably more hydrophilic. The fluid which comes into contact with such a structure will then experience a hydrophilicity gradient, thus creating a "driving" force in the direction of the absorbent core 24 provided by the surface finishes. This driving force is preferable to one provided by decreased pore size, since flow is directional without any impediment which may be caused by the decreased pore size in the "Z" direction.

The absorbent core 24 may be any absorbent means which is capable of absorbing or retaining liquids (e.g., menses and/or urine). As shown in FIGS. 1 and 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as creped polyester fibers; peat moss; tissue including tissue wraps and tissue laminates; absorbent foams; absorbent sponges; superabsorbent polymers; absorbent gelling material; or any equivalent material or combinations of material, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular-sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,67,8 issued to Weisman et at. on Sep. 9, 1986; U.S. Pat. No. 4,834,735 issued to Alemany et at. on May 30, 1989; U.S. Pat. No. 5,009,653 issued to Osborne on Apr. 23, 1991; and European Patent Application No. 0 198 683, The Procter & Gamble Company, published Oct. 22, 1986 in the name of Duenk et al. Each of these patents are incorporated herein by reference.

Alternatively, the absorbent core 24 may comprise a laminate structure comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et at. on Dec. 19, 1989; U.S. Pat. No. 4,822,543 issued to Dean et al. on Apr. 18, 1989; U.S. Pat. No. 4,889,595 issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al.; EPO Patent Application Publications Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The laminate may be formed of a sheet of cross-linked cellulosic fibers that wraps the layers of particles of absorbent gelling material. The sheet is wrapped so that it appears as having a "c" configuration when viewed from the end. The wrapped sheet forms an upper layer and a lower layer. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, cured, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibbers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

The backsheet 23 is impervious to liquids (e.g., menses and/or urine) and is preferably manufactured from a thin plastic film, although other flexible liquid impervious materials may also be use. As used herein, the term "flexible" refers to material which are compliant and will readily conform to the general shape and contours of the human body. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34 -2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs.

The flaps 34 serve at least two purposes. First, the flaps 34 help serve to prevent swelling of the wearer's body and panties by menstrual fluid, preferably by forming a double wall barrier along the edges of the panties. Second, the flaps 34 are preferably provided with attachment means on their garments surface so that the flaps 34 can be folded back under the panty and attached to garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 (i.e., unitary).

A number of sanitary napkins having flaps suitable or adaptable for use with the sanitary napkins of the present invention are disclosed in U.S. Pat. No. 4,687,478 entitled "Shaped Sanitary Napkin With Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Medingly on Aug. 26, 1986.

Figure 4:
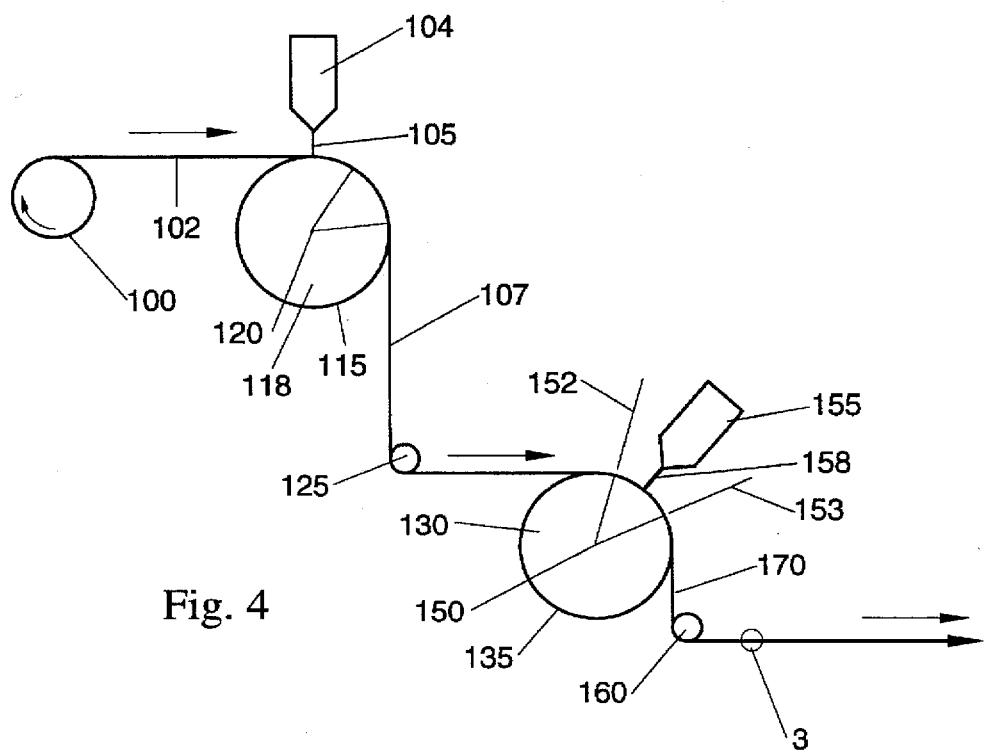
FIG. 4 is a simplified schematic illustration of a preferred process to form the web of the present invention.

FIG. 4 is a simplified, schematic diagram of a preferred process for producing three-dimensional, 102 macroscopically expanded, apertured, laminate webs of the present invention. A nonwoven web of lightly bonded fibers 102 is fed from supply roll 100 onto the surface of forming drum 118 about which a forming structure 115 continuously rotates. A web of molten resin 105 is extruded from a conventional extruder 104 onto nonwoven web 102. Forming structure 115 continuously rotates at substantially the same speed as the incoming web 102. The nonwoven web 102 having the molten resin 105 extruded thereon is driven by the forming drum 118.

Prior to being fed onto forming structure 115, nonwoven web 102 may be subjected to a ring rolling operation as known in the art. The ring rolling operation will effectively reduce the basis weight and bond strength of the nonwoven web.

Figure 5:
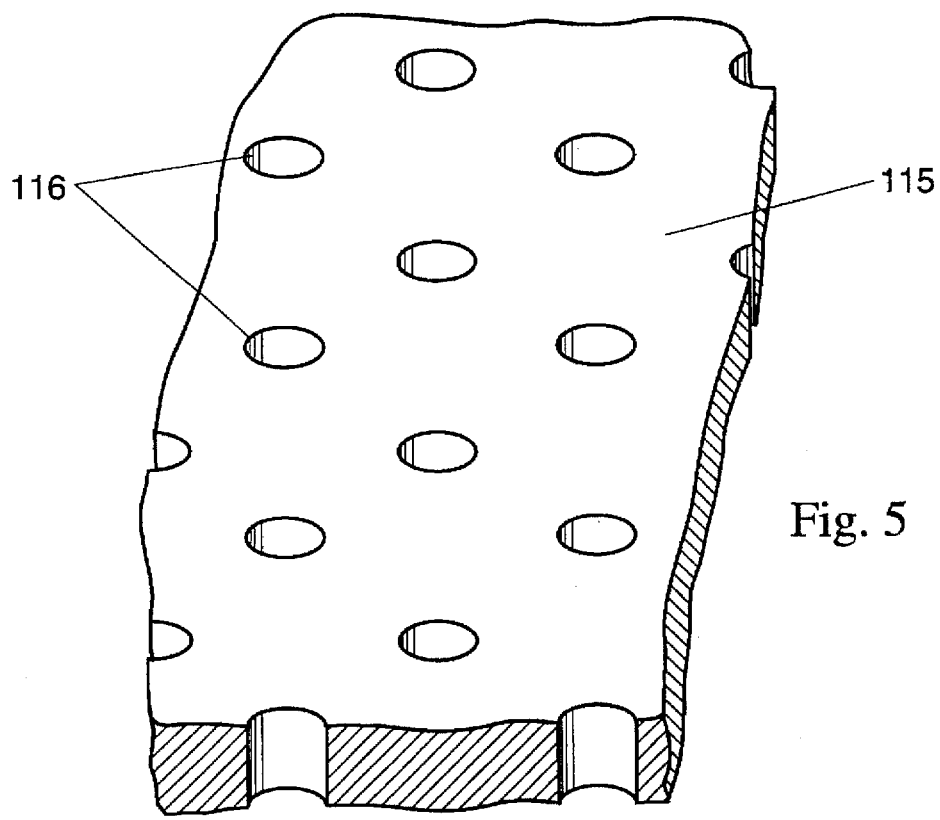
FIG. 5 is a greatly enlarged segmentary view of a forming structure used to carry out the forming process generally illustrated in FIG. 4.

Forming structure 115, a greatly enlarged fragmentary segment of which is illustrated in FIG. 5, includes a multiplicity of relatively small apertures 116 across all or any desired portion of its surface. Methods of constructing suitable three-dimensional tubular forming members of this general type are disclosed in commonly assigned U.S. Pat. No. 4,508,256 issued to Radel et al. on Apr. 2, 1985 and commonly assigned U.S. Pat. No. 4,509,908 issued to Mullane, Jr. on Apr. 9, 1985, said patents being incorporated herein by reference.

The apertures 116 in forming structure 115 may be of any desired shape or cross-section when the forming structure is fabricated using the laminar construction techniques generally disclosed in the aforementioned commonly assigned patents.

The forming drum 118 preferably includes an internally located vacuum chamber 120 which is preferably stationary relative to the moving forming structure 115. As the nonwoven web 102 and extruded molten resin 105 pass across the suction chamber 120, molten resin 105 is bonded or secured to nonwoven web 102 thus creating a substantially planar laminate 107. After having been formed on forming structure 115 laminate 107 is removed from forming structure 118 by an idler roll 125.

Figure 6:
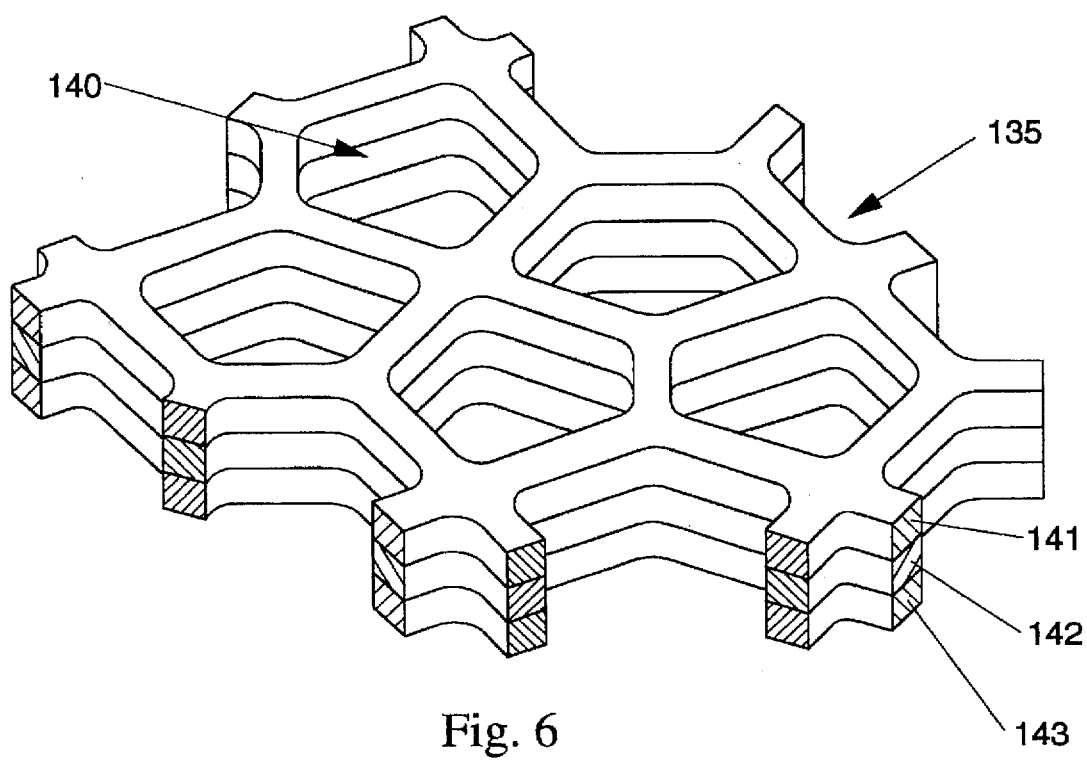
FIG. 6 is a greatly enlarged fragmentary view of a forming structure used to carry out the forming process generally illustrated in FIG. 4.

Having been removed from forming structure 118 by idler roll 125, laminate web 107 is fed onto the surface of forming drum 130 about which a forming structure 135 continuously rotates. Forming structure 135, a greatly enlarged fragmentary segment of which is illustrated in FIG. 6, includes a patterned network of pentagonally shaped capillaries 140. The forming structure is preferably constructed generally in accordance with the teachings of U.S. Pat. No. 4,342,314 issued to Radel and Thompson on Aug. 3, 1982 which is hereby incorporated herein by reference. Forming structure 135 is comprised of individual photoetched lamina 141, 142, and 143. A comparison of the forming structure 135 with the web 39 of FIG. 3 reveals the correspondence of the capillaries 40 in web 39 with the capillaries 140 in forming structure 135. The laminate structure is rolled by conventional techniques into a tubular forming structure.

The forming drum 130 preferably includes an internally located vacuum chamber 150 which is preferably stationary relative to the moving forming structure 135. A pair of stationary baffles 152, 153 approximately coinciding with the beginning and the end of the vacuum chamber 150 are located adjacent the exterior surface of the forming structure. Intermediate the stationary baffles 152,153 there is preferably provided means for applying a fluid pressure differential to the substantially planar laminate web 107 as it passes over the suction chamber. In the illustrated embodiment, the fluid pressure differential applicator means comprises a high-pressure liquid nozzle 155 which discharges a jet of liquid 158, such as water, substantially uniformly across the entire width of web 107. Examples of methods for the production of formed materials using a high-pressure liquid stream are disclosed in U.S. Pat. Nos. 4,695,422 issued to Curro et al. on Sep. 22, 1987; 4,778,644 issued to Curro et al. on Oct. 18, 1988; and 4,839,216 issued to Curro et al. on Jun. 13, 1989 all of which are hereby incorporated by reference.

The water jet causes the web 107 to conform to the forming structure 135 and apertures the web 107 in the areas coinciding with the capillaries 140 in forming structure 135.

Following application of the fluid pressure differential to the web, the apertured web 170 is removed from the surface of the forming structure 135 about an idler roll 160 in the condition illustrated in the inset of FIG. 3. The apertured web 170 may be utilized without further processing as a topsheet in an absorbent article. Alternatively, the apertured web 170 may be subjected to further processing, such as ring rolling, or surface treatment as may be desired.

Figure 7:
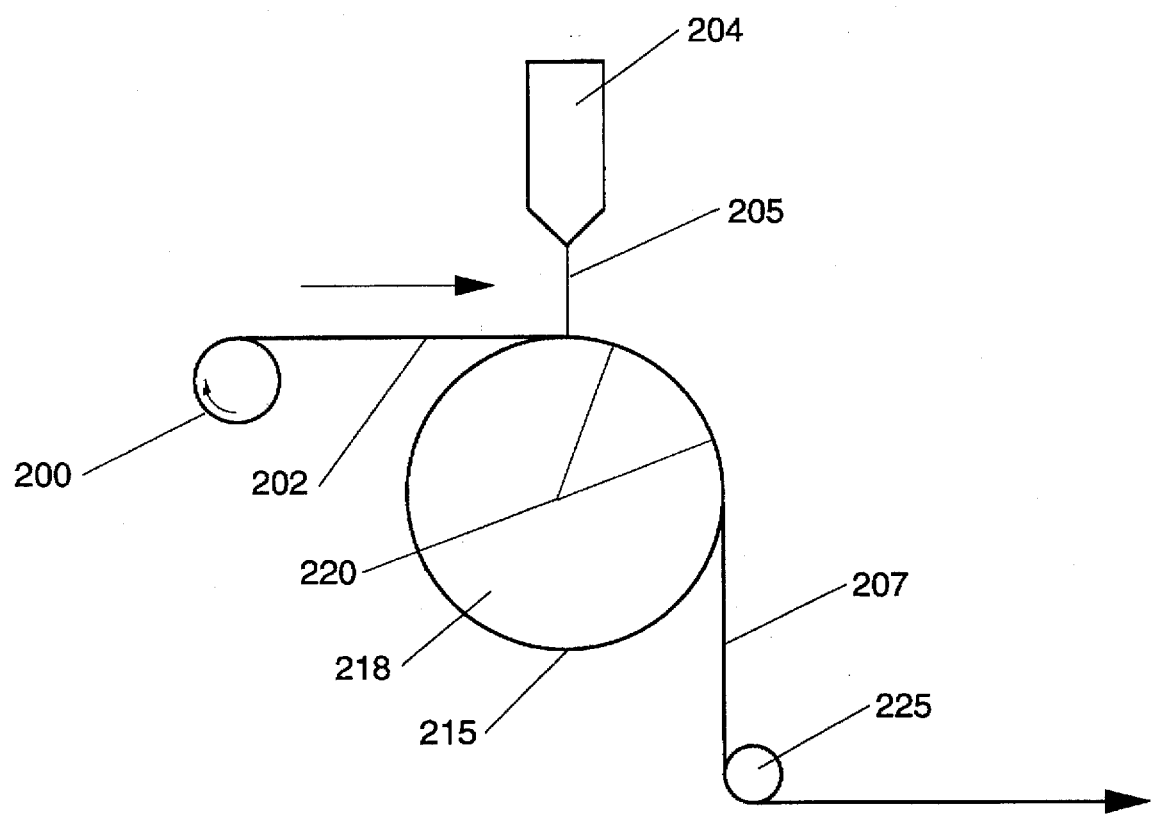
FIG. 7 is a simplified schematic illustration of another preferred process to form the web of the present invention.

FIG. 7 is a simplified schematic diagram of another preferred process for producing fibrous webs of the present invention. A nonwoven web of fibrous material 202 is fed from the supply roll 200 onto the surface of forming drum 218 about which a forming structure 215 continuously rotates. A web of molten resin 205 is extruded from a convention extruder 204 onto nonwoven web 202. Forming structure 215 continuously rotates at substantially the same speed as the incoming web. The nonwoven web 202 having the molten resin extruded thereon is driven by the forming drum 218.

The forming structure 215, is generally similar to the forming structure 135 shown in FIG. 6, which includes a patterned network of pentagonally shaped capillaries 140.

The forming drum 218 preferably includes an internally located vacuum chamber 220 which is preferably stationary relative to the moving forming structure 215. As the nonwoven web 202 and extruded resin 205 pass over vacuum chamber 220, the nonwoven web and molten resin are caused to conform with the forming structure 215 by the suction provided by vacuum chamber 220. The suction provided by vacuum chamber 220 is preferably great enough to aperture the nonwoven and molten resin web in the areas coinciding with the capillaries 140 in forming structure 135.

The resultant macroscopically expanded web 207 is generally similar to that shown in FIG. 3. After having been formed on forming structure 215 web 207 is removed from forming structure 215 by an idler roll 225.

Figure 8:
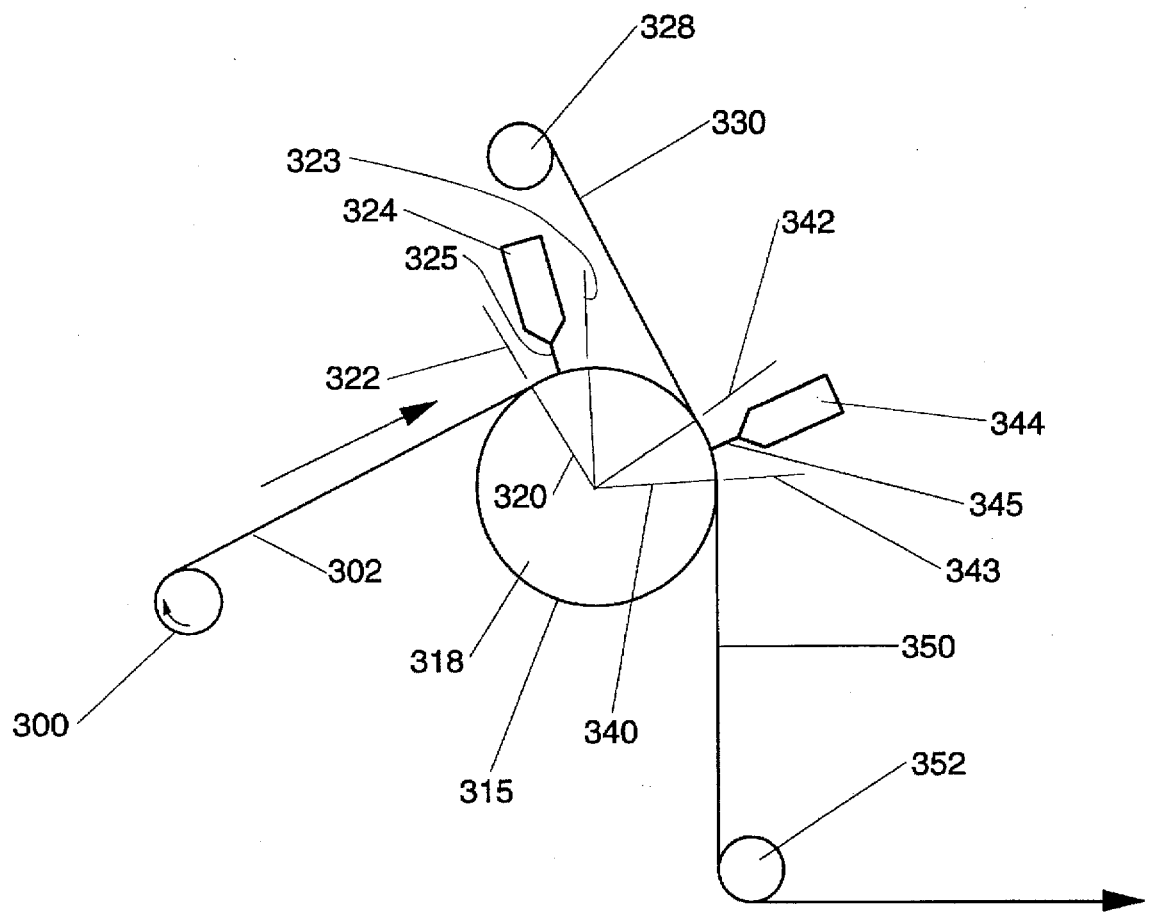
FIG. 8 is a simplified schematic illustration of another preferred process to form the web of the present invention.

FIG. 8 is a simplified schematic diagram of another preferred process for producing fibrous webs of the present invention. A nonwoven web of fibrous material 302 is fed from supply roll 300 onto the surface of forming drum 318 about which a forming structure 315 continuously rotates. Forming structure 315 continuously rotates at substantially the same speed as the incoming web. The nonwoven web 302 is driven by the forming drum 318. The forming structure 315, is generally similar to the forming structure 135 shown in FIG. 6, which includes a patterned network of pentagonally shaped capillaries 140. The forming drum preferably includes an internally located first vacuum chamber 320 which is preferably stationary relative to the moving forming structure 315. A pair of stationary baffles 322, 323 coinciding with the beginning and the end of the vacuum chamber 320 are located adjacent the exterior surface of the forming structure. Intermediate the stationary baffles 322, 323 there is preferably provided means for applying a fluid pressure differential to the incoming web 302 as it passes over the suction chamber. In the illustrated embodiment, the fluid pressure differential applicator means comprises a high-pressure liquid nozzle 324 which discharges a jet of liquid 325, such as water, substantially uniformly across the entire width of the web 302. The water jet causes the web 302 to conform to the forming structure 315 and apertures the web 302 in the areas coinciding with the capillaries in the forming structure.

Following application of the fluid pressure differential to the web, a web of planar polymeric material 330 is fed from supply roll 328 onto the formed and apertured web 302. Alternatively, a web of molten resin may also be extruded at this point from a conventional extruder onto the formed nonwoven web 302. The formed nonwoven web and polymeric material whether in planar or molten form is driven by the forming drum 315.

The forming drum 318 preferably includes an internally located second vacuum chamber 340 which is preferably stationary relative to the forming structure 315. A pair of stationary baffles 342, 343 approximately coinciding with the beginning and the end of the vacuum chamber 340 are located adjacent the exterior surface of the forming structure. Intermediate the stationary baffles 342, 343 there is preferably provided means for applying a fluid pressure differential to the nonwoven and polymeric web as it passes over the suction chamber. In the illustrated embodiment, the fluid pressure differential applicator means comprises a high-pressure liquid nozzle 344 which discharges a jet of liquid 345, such as water, substantially uniformly across the entire width of the web. The water jet causes the polymeric resin 330 to conform to the forming structure 315 and the already formed nonwoven web and apertures the polymeric resin 330 in the areas coinciding with the capillaries in the forming structure.

Following application of the fluid pressure differential to the web, the apertured web 350 is removed from the surface of the forming structure 315 by an idler roll 352. The apertured web 350 may be utilized without further processing as a topsheet in an absorbent article.

While particular embodiments of the present invention have been illustrated and described, it would be obvious to one skilled in the art that various other changes and modifications can be made without departing from the spirit and scope of the present invention. It is therefore intended to cover in the appended claims all such changes and modifications that are within the scope of this invention.

What is claimed is:

1. A three-dimensional, macroscopically expanded, fluid previous web suitable for use as a topsheet on an absorbent article, said web having a first surface and a second surface, said first surface and said second surface being located in planes remote from one another, said web comprising:
   (a) a first layer of substantially transparent, polymeric material, said first layer having an inner surface and an outer surface;
   (b) a nonwoven web secured to said inner surface of said first layer of substantially transparent polymeric material, said nonwoven web being visible through said first layer of substantially transparent polymeric material; and
   (c) a plurality of capillaries extending from said first surface of said web to said second surface of said web for the transmission of fluids through said web, each of said, capillaries originating-as an-aperture in said first surface of said web and having a continuously interconnected sidewall portion between said first and second surfaces, said continuously interconnected sidewall terminating to form an aperture in said second surface.

2. The web of claim 1, wherein said nonwoven web is thermally bonded to said first layer of substantially transparent, polymeric material.

3. The web of claim 1, wherein said first layer of substantially transparent, polymeric material is a co-extruded film.

4. The web of claim 1, wherein said nonwoven web comprises bi-component binder fibers.

* * * * *